US00RE38203E

(19) United States
(12) Reissued Patent
Kelly

(10) Patent Number: US RE38,203 E
(45) Date of Reissued Patent: Jul. 22, 2003

(54) EXTRACORPOREAL WHOLE BODY HYPERTHERMIA USING ALPHA-STAT REGULATION OF BLOOD PH AND $PCO_2$

(75) Inventor: Theodore C. Kelly, Minnetonka, MN (US)

(73) Assignee: First Circle Medical, Inc., Minneapolis, MN (US)

(21) Appl. No.: 09/415,902

(22) Filed: Oct. 7, 1999

Related U.S. Patent Documents

Reissue of:
(64) Patent No.: 5,674,190
Issued: Oct. 7, 1997
Appl. No.: 08/520,157
Filed: Aug. 28, 1995

(51) Int. Cl.[7] ..... A61M 35/00; A61F 7/00; A61B 19/00

(52) U.S. Cl. ..... 604/4.01; 607/106; 128/898

(58) Field of Search ..... 604/4.01, 6.13, 604/6.14, 6.16, 504, 506–8; 128/898; 607/106; 600/301, 529, 549, 483–84

(56) References Cited

U.S. PATENT DOCUMENTS 3,763,422 A * 10/1973 MacPhee et al.
4,266,021 A * 5/1981 Nylen et al. ..... 435/14
4,454,229 A * 6/1984 Zander et al. ..... 436/68
5,211,643 A * 5/1993 Reinhardt et al. ..... 604/416
5,354,277 A * 10/1994 Guzman et al. ..... 604/113
5,391,142 A * 2/1995 Sites et al. ..... 604/4.01
5,476,444 A * 12/1995 Keeling et al. ..... 604/4
5,630,413 A * 5/1997 Thomas et al. ..... 128/633
5,653,685 A * 8/1997 Klatz et al. ..... 604/26
5,928,180 A * 7/1999 Krivitski et al. ..... 604/4

FOREIGN PATENT DOCUMENTS

WO WO 95/10975 * 4/1995 ..... 604/65

OTHER PUBLICATIONS

*The American Journal of Medicine,* Aug. 1984, vol. 77, pp. 250–254, *Effects of Induced Total–Body Hyperthermia on Phosphorus Metabolism in Humans,* Kalpalatha K. Guntupalli, M.D., et al.*

*Surgery, Gynecology & Obstetrics,* Dec. 1982, vol. 155, pp. 897–912, *The Hydroxyl–Hydrogen Ion Concentration Ratio During Hypothermia,* Henry Swan, M.D.*

*Cardiothoracic Surgery Series,* Pathophysiology & Techniques of Cardiopulmonary Bypass, 1983 vol. II, pp. 40–48; *Carbon Dioxide Transport and Acid–Base Balance During Hypothermia,* Fred. N. White, Ph.D., Yitzhak Weinstein, Ph.D.*

(List continued on next page.)

*Primary Examiner*—Angela D. Sykes
*Assistant Examiner*—Patricia Bianco
(74) *Attorney, Agent, or Firm*—Popovich & Wiles, P.A.

(57) ABSTRACT

A device and method for extracorporeal whole body hyperthermia treatment of a patient's blood using alpha-stat regulation of blood pH and $pCO_2$ is described. The respiratory rate of a patient is either increased or decreased in accordance with the changes in pH, $pCO_2$, and base excess. The regulation of blood during the hyperthermic treatment of the patient's blood stabilizes the biochemical reactions fundamental to the metabolic welfare of the organisms within the patient's blood while the viruses within the patient's blood are eliminated.

18 Claims, 6 Drawing Sheets

OTHER PUBLICATIONS

*Medicine Watch,* May 28, 1995, pp. 1–2; *The Race Against Aids,* Sarah Richardson.*

*Cardiopulmonary Bypass;* 1991, pp. 48–52, Physiology Related Complications and Pharmacology, Casthley, P. Bergman, D. Futura Pub. Co.*

*The Journal of Extra–Corporeal Technology,* vol. 22, No. 3, Fall 1990. *Alpha–Stat versus pH–Stat: Implications for the Brain During Cardiopulmonary Bypass,* John M. Murkin, MD.*

*The Journal of Extra–Corporeal Technology,* vol. 17, No. 2, 1985. *Metabolic Rate, Temperature, and Acid–Base Control: The Best Strategy and Our Needs to Achieve It,* Henry Swan.*

*Cardiopulmonary Bypass Principles & Practice,* 1993, pp. 142–148, *Pathophysiology of Cardiopulmonary Bypass,* Davis, J. Utley.*

*The Practice of Cardiac Anesthesia,* Henstey, Martin, Little, Brown; 1990, pp. 610–613, Chp. 20, Pathophysiology of Cardiopulminary Bypass.*

Pathophysiology and Cardiopulmanary Bypass, pp. 145–157, *Hypothermia: Lessons From Comparative Physiology,* Fred N. White, Ph.D.*

*The Practice of Cardiac Anesthesia;* 1990, pp. 250–251; Henstey, Martin, Little, Brown, "Anesthetic Management During CPB".*

Pathophysiology, 1990, p. 406 "The Neurologic System".*

Frazier, "The Use of Hyperthermia in the Treatment of Cancer," *Proceedings of the American Academy of Cardiovascular Perfusion,* 3:99–104, (Jan. 1982).*

Scand. J. Thor. Cardiovasc. Surg 26: 1992, pp. 151–155, "Effect of Acid–Base Management With or Without Carbon Dioxide on Plasma Phosphate Conentration During and After Hypothermic Cardiopulmonary Bypass." Claude B. Kancir and Tommy Madsen.*

* cited by examiner

Amended Fig.2

Amended Fig.3

EXTRACORPOREAL WHOLE BODY HYPERTHERMIA USING ALPHA-STAT REGULATION OF BLOOD PH AND $PCO_2$

Matter enclosed in heavy brackets [ ] appears in the original patent but forms no part of this reissue specification; matter printed in italics indicates the additions made by reissue.

FIELD OF THE INVENTION

This invention relates generally to an apparatus and method for eliminating viruses by means of extracorporeal whole body hyperthermia, and more particularly to an apparatus and method that regulates the blood pH, $pCO_2$, and base excess, thereby maintaining a constant $CO_2$ as the patients body temperature is increased.

BACKGROUND OF THE INVENTION

The use of heat to treat ailments dates back many centuries to ancient Egyptian times, where certain cancers were treated by partial burial of the patient in hot sand. The use of hyperthermia as a treatment has continued into the twentieth century. Hyperthermia presents a unique set of physiologic problems that require careful management in order to achieve success. These problems have plagued soldiers on the battlefield, inner city residents during heat waves, and clinicians trying to treat cancer and AIDS.

In homoiothermal bodies, thermoregulation and maintenance of near normal temperature automatically takes precedence over other homeostatic functions, including electrolyte balance. In order to maintain normal temperatures during external exposure to heat, the body responds through an increase in both cardiac output, and more importantly, respiratory rate well above metabolic needs, thereby ridding the body of excess heat. The bulk of the blood is directed to the cutaneous vessels of the skin through increased cardiac output, while the increase respiratory rate or hyper ventilatory response is akin to the panting of a dog. A negative consequence of hyperventilation is that an increased respiratory rate effectively and drastically reduces the $pCO_2$ (and total $CO_2$) of the circulating blood creating a respiratory alkalosis. This decrease in $pCO_2$ increases the pH gradient across the cellular membrane. To regain electrical neutrality between intra and extracellular compartments there is a shift of ions between these two spaces, many of which may be lost due to renal excretion. Additionally, cellular function may be impaired as enzyme activity is adversely affected by electrolyte imbalance.

The measurement of intracellular pH has only been reliably performed within the last 25 to 30 years, therefore, most of this knowledge had gone unnoticed until 15 years ago. Researchers studying better methods of myocardial protection during hypthermic/cardioplegia cardiac arrest discovered that alkalotic infusion into the coronary arteries prior to the removal of the aortic cross clamp prevented the so called reperfusion injury.

During normal arterial blood flow, at 37° C. the arterial pH is approximately 7.4, having an arterial carbon dioxide tension of about 40 torr (mmHg). The human body modulates the arterial $pCO_2$ levels as temperature and the $CO_2$ content in the blood are altered. It is known that during hypothermic reactions, when the body temperature is decreased, there is a decrease in $pCO_2$ due to increased solubility, and increases in the blood pH. Generally, the $\Delta pH/°\ C. \cong -0.015$ when the $CO_2$ content of blood and the $[OH^-]/[H^+]$ remain constant. Also, pN is defined as the pH of the neutrality of water where $[H^+]+[OH^-]=1$, that is when ionic balance is achieved. This balance is governed by the ionization constant of water $K_w$ and varies with temperature. As temperature rises the pN is reduced. Of the three known buffer systems, it is believed that imidazole moiety of a person's blood accounts for this relationship.

Researchers in whole body hyperthermia have used temperature correction of blood gases (pH-stat). During the use of pH-stat, researches have observed electrolyte replacement and metabolic acidosis even with a reduced A—V $O_2$ difference. One explanation for this is that the use of the pH-stat technique artificially imposes a respiratory alkalosis which in turn affects oxyhemoglobin dissociation, reducing the availability of oxygen to the tissue.

In studies of heterotherms, or cold blooded animals, it was noted that as they were exposed and equilibrated to different temperatures, the $pCO_2$ values varied as the temperature dependent solubility factor changed, without concomitant alteration of total $CO_2$ content, which in turn resulted in an inverse change in pH. The misconception of homoiotherm (warm blooded) blood gas regulation insists that normality is based upon the blood pH of 7.40 and a $pCO_2$ of 40 torr and that changes of temperature do not effect this relationship. Indeed, pioneering work in cardiovascular surgery studied the effects of hypothermia on hibernating animals which maintain those values at lowered temperature. However, in the latter case hormonal and central nervous system intervention has affected the organism in ways which are not yet completely understood. In any case it is not the pH of the blood that is important, it is that of the intracellular space where the chemical reactions of life takes place.

Alpha-stat blood gas management achieved better methods of myocardial protection and was proposed for use during open heart surgery. Later, it was discovered that alpha-stat preserved the mechanisms of cerebral autoregulation, i.e. the appropriate blood flow rate for the metabolic needs of the brain. The practice of adding $CO_2$ to the blood in the oxygenator to maintain a normal temperature corrected $pCO_2$ (pH-stat) resulted in a blood flow exceeding demand as the $pCO_2$ is the controlling factor of cerebral autoregulation. The use of pH-stat regulation during hypothermic treatments produces a notable decrease in plasma phosphorous concentrations. Alternatively, the use of alpha-stat during total body hypothermia, reduces the amount of reduction in plasma phosphorous concentrations. The fact that alpha-stat may have an overall beneficial effect on human physiology, during hyperthermia, has largely gone unnoticed.

The properties of imidazole moiety of protein-bound histidine is described by White et al. in a paper entitled "Carbon Dioxide Transport and Acid-Base Balance During Hypothermia" (Pathophysiology & Techniques of Cardiopulmonary Bypass, 1983; Vol. II: 40–48). White et al. states that imidazole moiety is present in a persons blood in sufficient quantity to account for the pH-temperature relationship. The state of protonization (charged state) of imidazole is expressed as a variable (alpha) equal to the ratio of deprotonated to total imidazole groups. White et al. notes that the maintenance of a constant alpha, referred to as [alpha-star] *alpha-stat* behavior, occurs when carbon dioxide partial pressure ($pCO_2$) is appropriately regulated by ventilation. During a decrease in temperature (hypothermia), the maintenance of arterial blood at constant $CO_2$ content is achieved either by reducing the base excess of the blood or elevating $pCO_2$ as a function of temperature. Claude B. Kancir and Tommy Madsen in an article entitled Effect of Acid-Base Management With or Without Carbon Dioxide on Plasma Phosphate Concentration During And After Hypothermic Cardiopulmonary Bypass; Scand J Thor Cardiovasc Surg. 151–155, 1992, concluded that "acid-base management may influence phosphate homeostasis during hypothermia for cardiac surgery."

As recognized in Sites et al. U.S. Pat. No. 5,391,142, hyperthermic treatment of a patient's blood has been well accepted as a cancer treatment. Sites et al. recognized that the hyperthermic treatment of blood could be used to treat for cancer, acquired immune deficiency syndrome (AIDS), collagen vascular diseases such as rheumatoid arthritis and scleroderma, hepatitis, and Epstein-Barr virus. Sites et al. did not, however, recognize the need to regulate the biochemical reactions fundamental to the metabolic welfare of the organisms within a patient's blood while the viruses within the patient's blood are eliminated.

During hyperthermia, $pCO_2$ varies directly with a change in body temperature. It is desirous to hold the bloods $CO_2$ content constant during alpha-stat regulation, thereby requiring an inverse relationship between air convection requirements and body temperature. [Alpha-star] *Alpha-stat* maintains constant $CO_2$ by regulating $pCO_2$. Hence, utilizing the alpha-stat technique for blood gas-management is advantageous in that the pH gradient across the cellular membrane is preserved throughout the range of temperatures encountered during hyperthermia.

The present invention includes an apparatus and method for use in performing extracorporeal whole body hyperthermia maintaining a constant $CO_2$ content by regulating the pH, $pCO_2$, and base excess of the blood. The apparatus and method consolidate and coordinate components used in treatments. They, thereby, address many of the dictates and solve many of the problems of the related art.

SUMMARY OF THE INVENTION

The problems alluded to above are solved in accordance with the present invention by providing an apparatus and method for extracorporeal hyperthermic treatment of a patient's blood. By direct control of pulmonary ventilation through manipulation of respiratory rate, the $pCO_2$, the total $CO_2$, and the pH can be maintained throughout the procedure according to alpha-stat parameters, ensuring that electrolyte balance is maintained throughout. In a recent clinical trial of 6 AIDS patients at 41° to 42° C. for up to 220 min., this technique was implemented with outstanding results. No electrolyte replacement was required in any patient during the procedure, nor was there ever a need to administer sodium bicarbonate for metabolic acidosis.

The apparatus of the present invention consists of a blood flow circuit which is cannulated to the patient. The blood flow circuit comprises several noncontinuous conduits coupled in series to the following: a Blood Gas Analyzer (BGA) or probes connected to a BGA, pump, pressure transducer, heat exchanger, temperature probe, filter, flow probe, and clamps. If desired, the entire flow circuit could be a disposable unit, whereby a medical treatment facility could inhibit the possibility of contamination of the blood of one patient by the blood of another patient previously treated (cross-contamination). A blood flow circuit, similar to the blood flow circuit described by Sites et al. in U.S. Pat. No. 5,391,142 may be used, the description of which is incorporated herein by reference.

A motor which drives the pump is coupled physically to the pump and electrically to a microprocessor. The microprocessor controls the speed of the motor and consequently the rate the blood is pumped through the flow circuit. The BGA may be linked to the microprocessor or may be a stand alone unit. The microprocessor is also connected to the heat exchanger, thereby allowing the operator to vary the temperature of the blood. Leads from the temperature probe, flow probe, and pressure transducer are connected to an analog/digital converter which is coupled to the microprocessor. The microprocessor utilizes the information from the probes, transducer and BGA is controlling the motor and heat exchanger.

Within the BGA is an analyzer which analyzes the blood gases, including the blood pH and $pCO_2$ through infra-red or chemical analysis. A pulse oximeter attached to the patient through suitable means, measures the $pO_2$ of a patient's blood. The microprocessor then analyzes the data associated with the blood's pH, $pCO_2$, $pO_2$ and calculates the base excess of the blood normalized at 37° C. The microprocessor is programmed to then automatically adjust the respiratory rate of the patient and either the amount of $NaHCO_3$ or acidotic crystalloid solution (which affects the $HCO_3^-$ ion concentration) being introduced into the patient's blood. This may be accomplished by adjusting the respiratory rate of the patient through ventilation or medications.

The respiratory management of the blood at constant $CO_2$ content, while the temperature is changed, maintains a constant alpha thereby stabilizing the biochemical reactions fundamental to the metabolic welfare of organisms within the patient's blood. The sodium bicarbonate buffering system is based upon the following equation:

$$H^+ + HCO_3^- \sim H_2CO_3 \sim H_2O + CO_2$$

Acidosis (↓pH) occurs when there is an increase of $H^+$ (metabolic) and/or $CO_2$ (respiratory). Respiratory acidosis is treated with changes in depth of ventilation or ventilatory rate. Metabolic acidosis is treated with the administration of sodium bicarbonate ($NaHCO_3$). "Bicarb" dissociates into Na+ and $HCO_3^-$ which combines with $H^+$ to form $CO_2$ and $H_2O$.

The blood gases, pH, $pO_2$, $pCO_2$, and $HCO_3^-$ concentration are obtained by direct measurement. Base excess (BE) is a derived parameter based upon the relationship between the measured $pCO_2$, and $HCO_3^-$ concentration, and is calculated relative to the normal $HCO_3^-$ concentration values: 24 mEq/L in arterial blood and 26 mEq/L in venous blood.

It is accordingly a principal object of the present invention to remove viruses from a patient's blood through extracorporeal hyperthermia while regulating the acid-base equilibrium of the patient's blood as the patient's body temperature is changed.

Another object of the present invention is to provide a method of treating the patient's blood during extracorporeal hyperthermic treatment, whereby, the biochemical reactions fundamental to the metabolic welfare of the organisms in a patient's blood is stabilized.

Yet another object of the present invention is to provide an economical apparatus for the hyperthermic treatment of blood which regulates the patients blood to keep the acid-base equilibrium of the blood constant, wherein all components in contact with the patient's blood are disposable.

These and other objects and advantages as well as these and other features will become apparent to those skilled in the art from the following detailed description of a preferred embodiment of the invention, especially when considered in conjunction with the accompanying drawings in which like numerals in the several view refer to corresponding parts.

DETAILED DESCRIPTION OF THE PREFERRED EMBODIMENT

Figure 1:
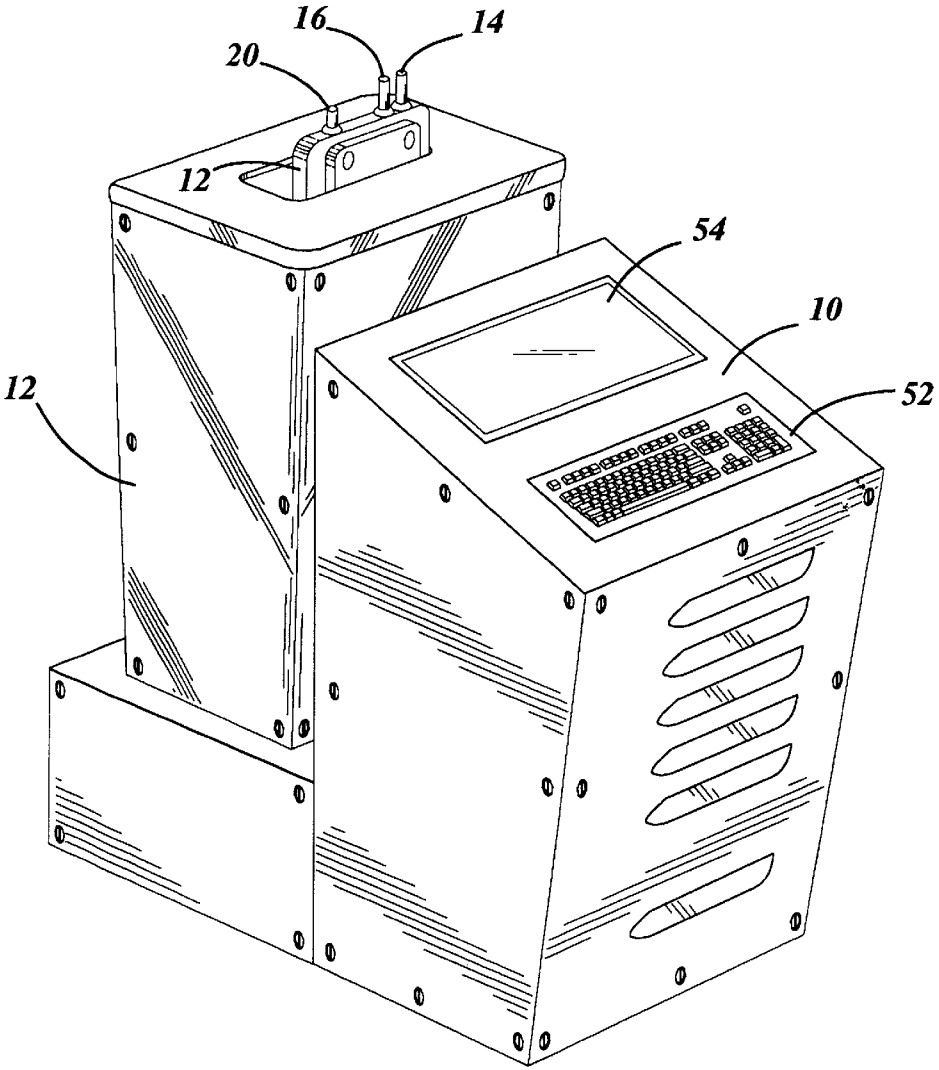
FIG. 1 is a simplified perspective view of the present device for extracorporeal treatment of a patient's blood to combat viruses therein.

Referring first to FIG. 1, there is shown generally a blood treatment console 10 and a blood flow circuit module 12. The blood flow circuit module 12 consists of an input conduit 14, an output conduit 16, a plurality of leads joined at an electrical connector 20 and the following components coupled by conduit segments 21 in series: a BGA 22, a pump 24, a heat exchanger 26, one or more temperature probes 28, a flow probe 30, a pressure transducer 32 and a filter 34 (see FIG. 2). A motor 25 is physically connected to pump 24 and electrically connected to microprocessor 50. Within the BGA 22 is an infra-red analyzer or chemical analyzer (not shown) of known construction for determining the blood gases and pH of the blood. Electrical leads 38–46 extend from the BGA 22, pump 24, heat exchanger 26, temperature probe 28, flow probe 30, and pressure transducer 32. These electrical leads all connect to the central electrical connector 20 which sealably extends from the blood flow circuit module 12. Corresponding leads couple the electrical connector 20 to an analog/digital converter 48 which, in turn, is coupled to the microprocessor 50.

The microprocessor 50 is built into the console 10 and has a keyboard 52 for input and a monitor 54 to display an output. The microprocessor 50 is further coupled by electrical leads 39, and 58–62 in controlling relation to an intravenous (IV) drip 70, pulse oximeter 68, and a ventilator 66 the arrows on the lines illustrating electrical leads 39 and 58–62 are provided to indicate the direction of flow of the electrical signal transmitted through the corresponding lead. The ventilator 66 is shown coupled to the patient with arrows indicating the direction of respiratory flow. The IV drip further has a multi-port line 64 allowing varying medications, etc. to be administered. The arrow on multi-port line 64 indications the direction of flow of the varying medications from the IV drip 70. The microprocessor 50 may be programmed to control the rate of the motor 25, the temperature level of the heat exchanger 26, the respiratory rate controlled by the ventilator 66, and the $NaHCO_3$ in the blood administered through the IV drip 70. The BGA 22 or microprocessor 50 determines the base excess from the $pCO_2$, $pO_2$ and pH of the patient's blood and accordingly adjusts the $NaHCO_3$ administered to the patient through the IV drip 70.

The Base Excess is calculated by:

1. Normal Bicarb: Arterial =24 mEq/L; Venous=26 mEq/L;
2. if ↑ $pCO_2$, Add 1 mEq/L for every 10 torr above 40; if ↓ $pCO_2$, Subtract 1 mEq/L for every 5 torr below 40 (this gives the anticipated bicarb level);
3. From anticipated bicarb, add/subtract actual (measured) bicarb; the result is the base excess or deficit.

The following examples will further clarify the Base Excess/Deficit calculation:

EXAMPLE 1

Given that the Arterial blood gas pH=7.5, $pCO_2$=25, and $HCO_3^-$ concentration=16

1. Normal arterial bicarb=24 mEq/L
2. $pCO_2$ is decreasing, therefore subtract −3 mEq/L; Hence, anticipated bicarb=21 mEq/L
3. (anticipated bicarb=21)−(measured bicarb=16)=5 mEq/L base deficit

EXAMPLE 2

Given that the Venous blood gas pH=7.1, $pCO_2$=50, and $HCO_3^-$ concentration =12

1. Normal [arterial] *venous* bicarb=26 mEq/L
2. $pCO_2$ is increasing, therefore add 1 mEq/L; Hence, anticipated bicarb=27 mEq/L
3. (anticipated bicarb=27)−(measured bicarb=12)=15 mEq/L base defecit or −15 mEq/L base excess A negative base excess, sometimes referred to as base deficit indicates metabolic acidosis and is treated with Sodium bicarbonate ($NaHCO_3$). A positive base excess indicates metabolic alkalosis which is generally not seen during extracorporeal circulation but can occur due to over use of bicarb and can be treated by the use of a slightly acidotic crystalloid solution such as Normal Saline (0.09% NaCl) solution Generally a base excess of 0±3 mEq/L is clinically acceptable and no action is normally taken. When the base excess exceeds these values, the following action is taken. When there is a base deficit, the extracellular fluid (ECF) [volume×Base deficit=Dose of $NaHCO_3$, where] the ECF= approximately 20% of body weight, therefore 0.2×BD= $NaHCO_3$. When there is a base excess, the operator switches IV solutions, or it may be switched automatically. With adequate urine output, patients undergoing whole body hyperthermia require approximately 1000 ml/hr of crystalloid solution to make up for fluid losses due to urine, sweat and respiration. Normally this solution is a balanced electrolyte solution with a physiological pH. During the correction of metabolic alkalosis the rate and volume of the substituted solution should not be changed.

Figure 2:
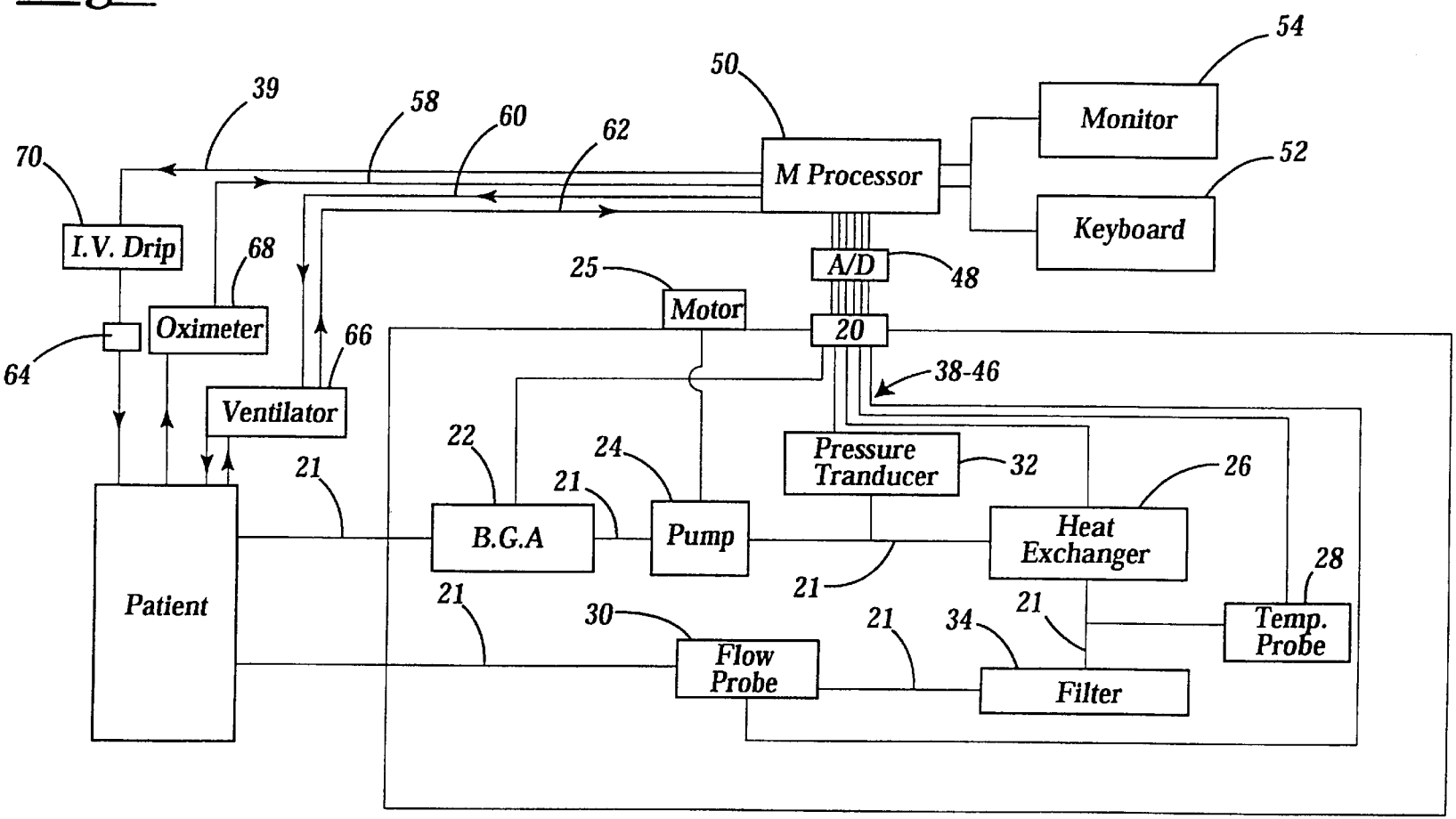
FIG. 2 is a block diagram of one embodiment of the equipment employed in carrying out the invention.
Figure 3:
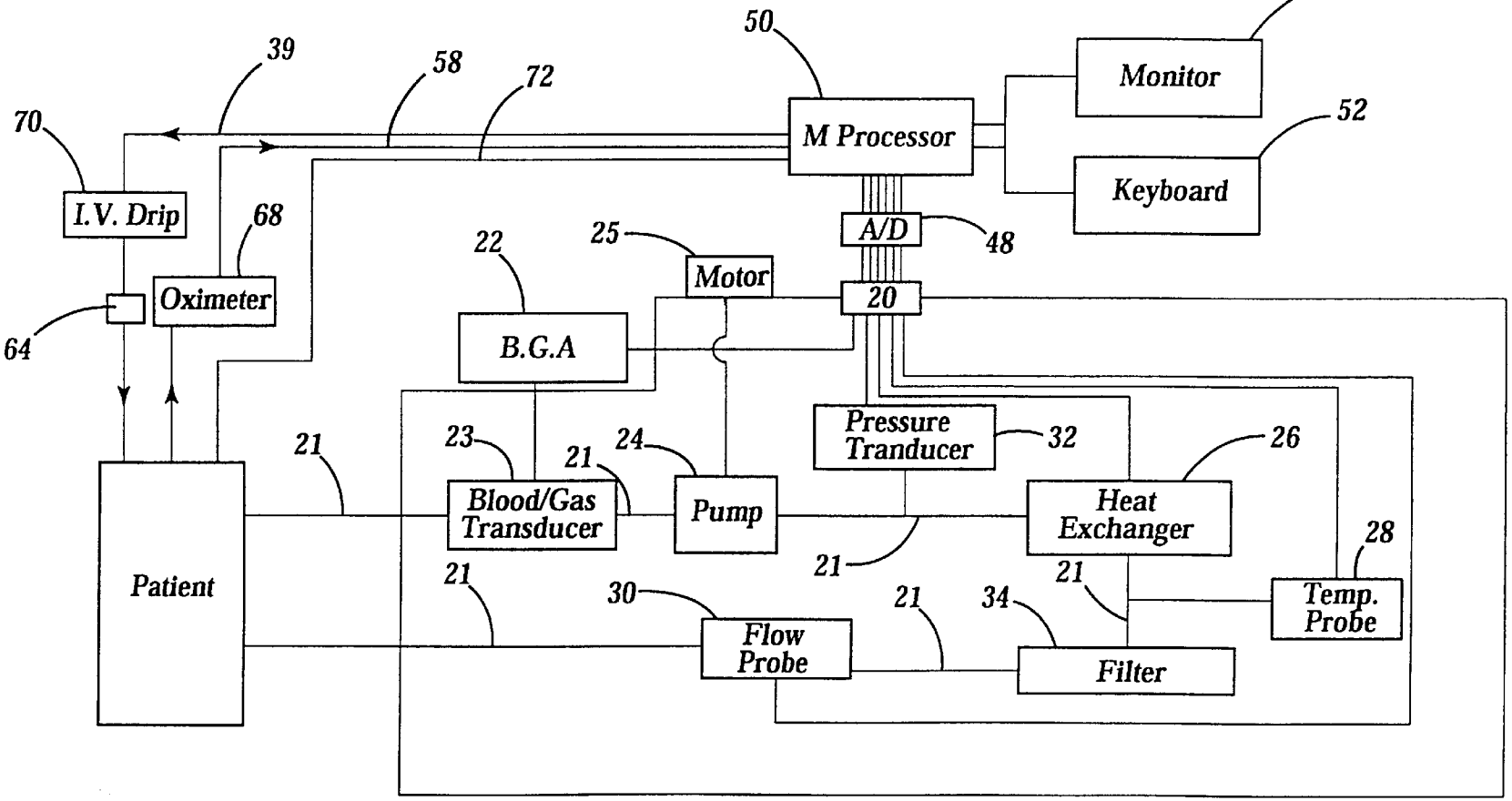
FIG. 3 is a block diagram of another alternate preferred embodiment of the equipment employed in carrying out the invention.

Referring next to FIG. 2, a block diagram of the components of the module 12 and console 10 are shown coupled to the patient, ventilator 66, oximeter 68, and IV drip 70. The pulse oximeter probe 68 is attached to the patient the arrow on the attachment line indicates the direction of an electrical signal transmitted by the oximeter probe 68 continuously asses the $pO_2$ of the patient's blood. FIG. 3 shows in block diagram the module 12 and console 10 coupled to the patient similar to that shown in FIG. 2, wherein the patient's blood flows in series through BGA 22, through pump 24, past pressure transducer 32, through heat exchanger 26, past temperature probe 28, through filter 34, past flow probe 30, and back to the patient. The primary difference between the embodiments of FIGS. 2 and 3 is that in FIG. 3 the patient's respiratory rate is not controlled by a ventilator 66, and the BGA 22 is outside the module 12. Blood gas transducers or probe 23 are contained within the module 12. An electrical lead 72 is shown connected from the patient to the microprocessor 50. A signal is sent to the microprocessor 50 corresponding to the respiratory rate of the patient. This electrical lead 72 may alternatively be linked with the pulse oximeter probe 68. A medication for affecting a patient's respiratory rate is administered through the IV drip 70, whereby the amount administered may be controlled manually or by the microprocessor 50. A short acting narcotic is preferably used as a respiratory suppressant. Narcotics have less tendency to have an affect on the acid base equilibrium of the blood, and their effects are easily reversed.

Figure 4:
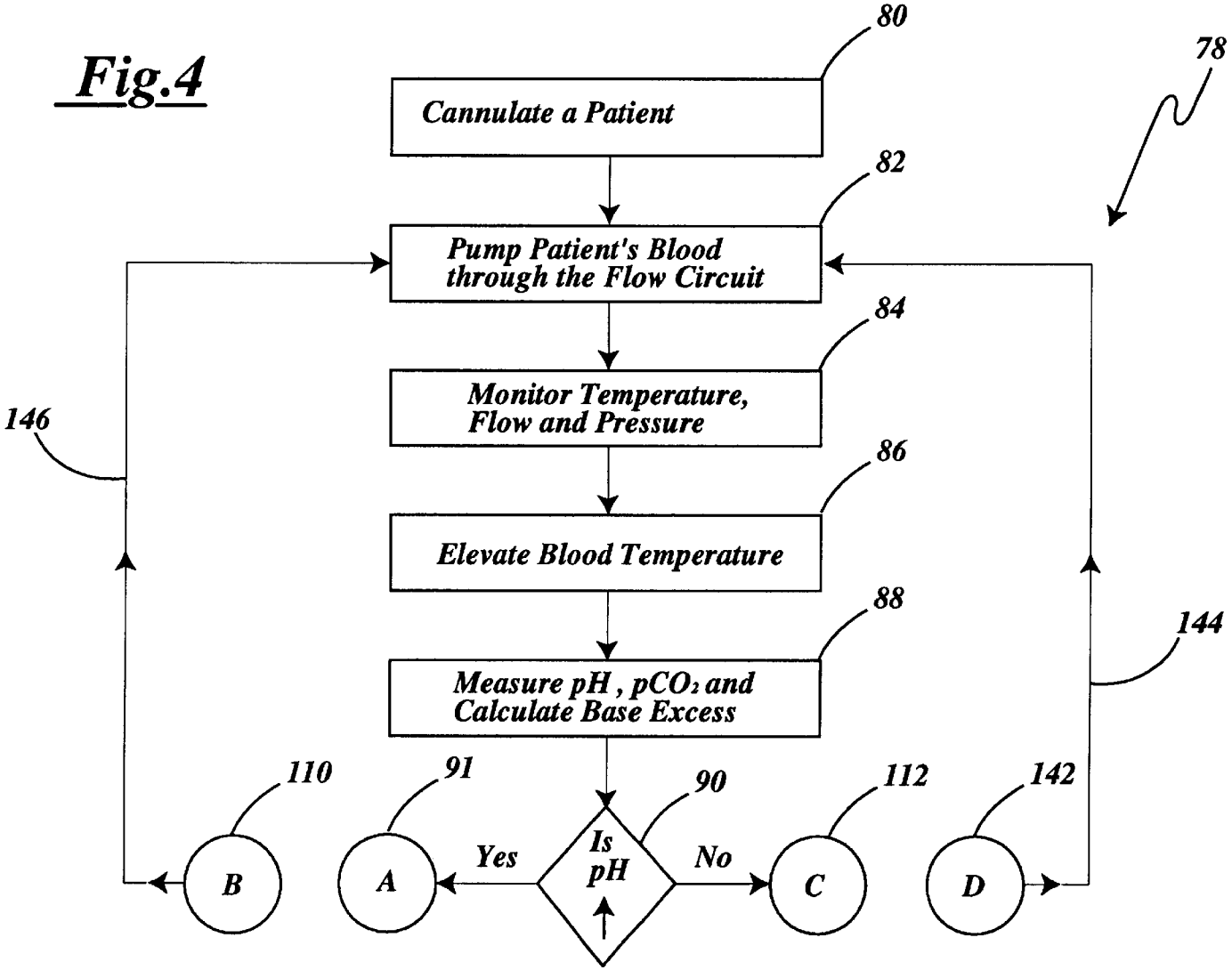
FIGS. 4–6 is a software flow diagram of the process of extracorporeal hyperthermic treatment of a patient's blood to combat viruses therein, incorporating an alpha-stat protocol.
Figure 5:
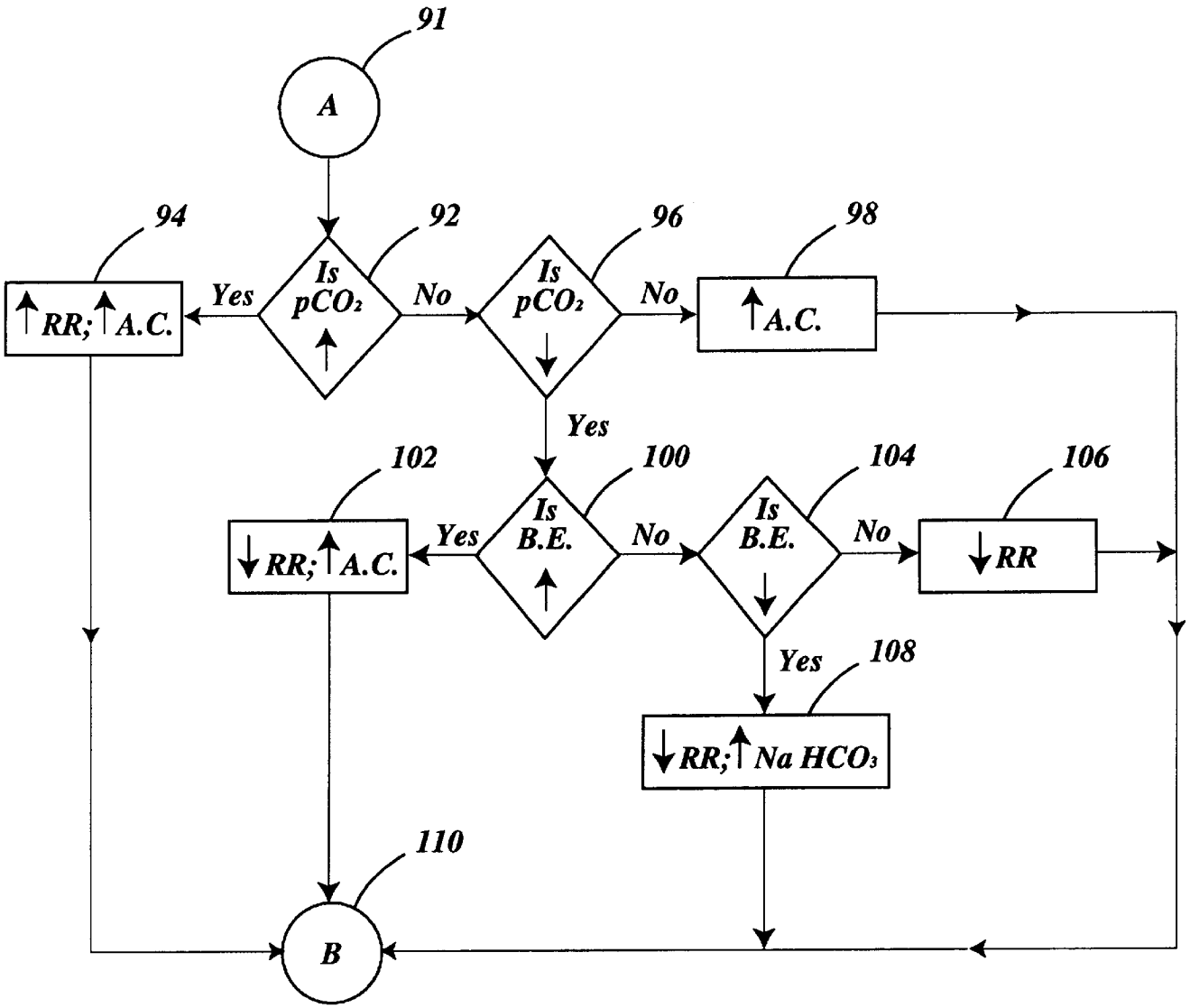
Figure 6:
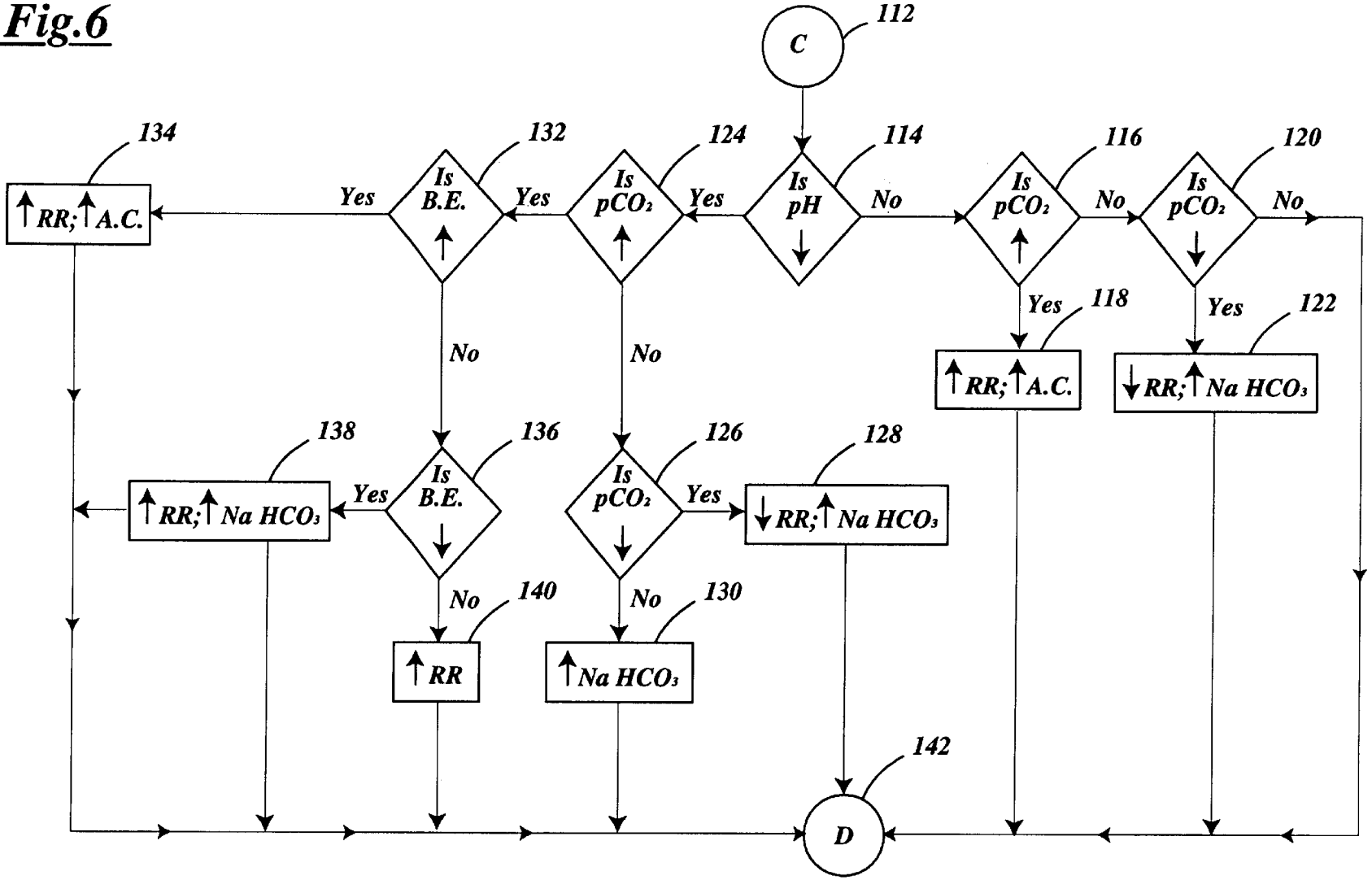

Referring now to FIGS. 4–6, the steps the microprocessor takes in controlling the respiratory rate of a patient, $HCO_3^-$ ion concentration in the patient's blood, and amount of acidotic crystalloid, so as to incorporate the alpha-stat protocol, is shown in a flow chart 78. The legend ["↓"] "↑" represents an increase or addition and the legend "↓" represents a decrease or reduction. The legend "RR" represents the respiratory rate, the legend "AC" represents the acidotic Crystalloid, "$NaHCO_3$" represents sodium bicarbonate. A decision chart shown in Table 1 further exemplifies the varying action that is taken in response to variation in the pH, $pCO_2$, and Base Excess. Persons skilled in programming can readily devise the necessary object code and/or source code for a given microprocessor to implement the operations depicted in the flow chart 78.

TABLE 1

| When the pH is _, and | when the $pCO_2$ is _, and | when the Base Excess is _, | take the following action: |
|---|---|---|---|
| ↑ | ↑ | ↑ | ↑RR, +AC |
| ↑ | no change | ↑ | +AC |
| ↑ | ↓ | ↓ | ↓RR, +$NAHCO_3$ |
| ↑ | ↓ | no change | ↓RR |
| ↑ | ↓ | ↑ | ↓RR, +AC |
| no change | ↑ | ↑ | ↑RR, +AC |
| no change | no change | no change | No Action |
| no change | ↓ | ↓ | ↓RR, +$NAHCO_3$ |
| ↓ | ↑ | ↑ | ↑RR, +AC |
| ↓ | ↑ | no change | ↑RR |
| ↓ | ↑ | ↓ | ↑RR, +$NAHCO_3$ |
| ↓ | no change | ↓ | +$NAHCO_3$ |
| ↓ | ↓ | ↓ | ↓RR, +$NAHCO_3$ |

During extracorporeal hyperthermic treatment of the blood, a patient must first be cannulated (block 80). The patient's blood is then pumped through the extracorporeal blood flow circuit 12 (block 82), wherein the temperature, rate of flow and pressure are monitored (block 84). As the blood's temperature is elevated (block 86), so to is the patient's body temperature. The blood pH, $pCO_2$, and base excess are continuously measured and normalized to read values at 37° C. and then the base excess is calculated (block 88).

If the blood pH is found to be increasing (decision block 90 and connector 91), a determination is made at decision block 92 whether the $pCO_2$ is increasing. If the test shows that $pCO_2$ is increasing the microprocessor 50 sends a signal to the ventilator 66 to incrementally increase the respiratory rate and infuse an acidotic crystalloid solution, such as normal saline (block 94). If the $pCO_2$ is not increasing a determination is made whether the $pCO_2$ is decreasing (decision block 96). If the $pCO_2$ is not decreasing, the amount of acidotic crystalloid is increased (block 98). If the $pCO_2$ is decreasing, a determination is made whether the base excess is increasing (decision block 100). If the base excess is increasing, the respiratory rate of the patient is decreased and acidotic crystalloid is increased (block 102). If the base excess is not increasing a determination is made whether the base excess is decreasing (decision block 104). If the base excess is not decreasing the respiratory rate is decreased (block 106). If the base excess is decreasing the respiratory rate is decreased and an amount of $NaHCO_3$ is added (block 108). The process then loops back through connector 110, to pumping more blood through the flow circuit (block 82).

If the test at block 90 shows that the blood pH is not increasing, it is then determined whether the pH is decreasing (C connector 112 and decision block 114). If the pH is not decreasing a determination is made whether the $pCO_2$ is increasing (decision block 116). If the $pCO_2$ is increasing the respiratory rate is increased and an amount of acidotic crystalloid is added (block 118). If the $pCO_2$ is not increasing at decision block 116, it is then determined whether the $pCO_2$ is decreasing (decision block 120). If the $pCO_2$ is decreasing, the respiratory rate is decreased and an amount of $NaHCO_3$ is added (block 122). If it is determined at decision block 120 that the $pCO_2$ is not decreasing, then no change is made and the process loops back to pumping more blood into the flow circuit (block 82).

If the decision at block 114 indicates that the pH is decreasing, a determination is then made whether the $pCO_2$ is increasing (decision block 124). If the $pCO_2$ is not increasing, it is determined whether the $pCO_2$ is decreasing (decision block 126). If the $pCO_2$ is decreasing the respiratory rate is decreased and an amount of $NaHCO_3$ is added (block 128); if the $pCO_2$ is not decreasing an amount of $NaHCO_3$ is added (block 130). The process then loops back through connector D.

If a determination at decision block 124 was made that the $pCO_2$ was increasing, a determination is then made whether the base excess is increasing (decision block 132). If the base excess is increasing, the respiratory rate is increased an amount of acidotic crystalloid is added (block 134). If the base excess is not increasing at decision block 132, it is then determined whether the base excess is decreasing (decision block 136). If the base excess is decreasing, the respiratory rate is increased and an amount of $NaHCO_3$ is added (block 138); if the base excess is not decreasing the respiratory rate is increased (block 140). The process then loops back to pumping blood into the flow circuit (82) through connector 142. The microprocessor 50 continuously regulates the $pCO_2$, pH, and base excess keeping the $CO_2$ content constant while the patient's blood temperature changes above 37° C. (loops 144 and 146).

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. A method of extracorporeal treatment of a patient, comprising the steps of:

(a) cannulating a patient for extracorporeal blood circulation wherein a blood flow circuit is defined between a first point of cannulation and a second point of cannulation;

(b) then pumping a patient's blood through the blood flow circuit;

(c) monitoring a patient's temperature, blood pressure, and a flow rate of blood as the patient's blood passes through the blood flow circuit;

(d) as the patient's blood is monitored, heating the patient's blood in the blood flow circuit to an elevated temperature; then (e) measuring blood pH, partial pressure of $CO_2$ gas in the patient's blood ($pCO_2$), and $HCO_3^-$ concentration in the patient's blood;

(f) calculating a base excess from the pH, $pCO_2$, and $HCO_3^-$ concentration of the patient's blood measured in step (e); and then (g) adjusting a respiratory rate of the patient and administration of a concentration of $NaHCO_3$ in the patient's blood as a function of at least one of a change in the blood pH, a change in the $pCO_2$, and a change in the base excess.

2. The method as in claim 1, wherein the step of adjusting a respiratory rate of the patient comprises decreasing said respiratory rate when at least one of an increase in blood pH, a decrease in $pCO_2$ and an increase in the base excess is determined from steps (e) and (f).

3. The method as in claim 1, wherein the step of adjusting a respiratory rate of the patient comprises decreasing said respiratory rate when at least one of a decrease in blood pH, a decrease in $pCO_2$ and a decrease in the base excess is determined from steps (e) and (f).

4. The method as in claim 3, further comprising the step of increasing the $HCO_3^-$ ion concentration when the base excess of the patient's blood calculated in step (f) is determined to be decreasing with a change in body temperature of the patient.

5. The method as in claim 1, wherein the step of adjusting a respiratory rate of the patient comprises increasing said respiratory rate when at least one of a decrease in blood pH, an increase in $pCO_2$ and a decrease in the base excess is determined from steps (e) and (f).

6. The method as in claim 5, further comprising the step of increasing the $HCO_3^-$ ion concentration when the base excess of the patient's blood calculated in step (f) is determined to be decreasing with a change in body temperature of the patient.

7. The method as in claim 1, wherein the step of adjusting the respiratory rate of the patient comprises increasing said respiratory rate when an increase in blood pH, an increase in $pCO_2$ and an increase in the base excess is determined from steps (e) and (f).

8. The method as in claim 1, wherein the step of adjusting administration of a concentration of $NaHCO_3$ comprises increasing the concentration of $NaHCO_3$ when the base excess is determined to be decreasing as the patients body temperature is raised.

9. The method as in claim 1, further comprising the step of increasing a concentration of acidotic crystalloid when the base excess of the patient's blood is determined to be increasing with a change in body temperature of the patient.

*10. A method of extracorporeal treatment of a patient comprising:*

*(a) circulating the patient's blood from the patient through an extracorporeal blood flow circuit, and back to the patient, wherein the blood returned to the patient has been heated within the blood flow circuit to an elevated temperature range;*

*(b) measuring blood pH, partial pressure of $CO_2$ gas in the patient's blood ($pCO_2$), and $HCO_3^-$ concentration in the patient's blood;*

*(c) calculating a base excess from the pH, $pCO_2$, and $HCO_3^-$ concentration of the patient's blood measured in step (b); and*

*(d) adjusting a respiratory rate of the patient and administration of a concentration of $NaHCO_3$ in the patient's blood as a function of at least one of a change in the blood pH, a change in the $pCO_2$, and a change in the base excess.*

*11. The method as in claim 10, wherein the $pCO_2$ of the blood is normalized at 37° C.*

*12. The method as in claim 10, wherein the base excess is normalized at 37° C.*

*13. The method as in claim 10, wherein the pH is normalized at 37° C.*

*14. The method as in claim 10, wherein the respiratory rate of the patient is adjusted as a function of a change in the $pCO_2$ of the blood.*

*15. The method as in claim 10, wherein the administration of a concentration of $NaHCO_3$ in the patient's blood is adjusted as a function of a change in the base excess.*

*16. The method as in claim 10, wherein the respiratory rate of the patient is adjusted as a function of a change in the $pCO_2$ of the blood and the administration of a concentration of $NaHCO_3$ in the patient's blood is adjusted as a function of a change in the base excess.*

*17. The method as in claim 10, wherein the respiratory rate of the patient is adjusted through ventilation.*

*18. The method as in claim 10, wherein the respiratory rate of the patient is adjusted through medications.*

* * * * *